United States Patent
Allen, IV (10) Patent No.: US 10,517,665 B2
(45) Date of Patent: Dec. 31, 2019

(54) DEVICES AND METHODS FOR TISSUE SEALING AND MECHANICAL CLIPPING

(71) Applicant: COVIDIEN LP, Mansfield, MA (US)

(72) Inventor: James D. Allen, IV, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 373 days.

(21) Appl. No.: 15/627,571

(22) Filed: Jun. 20, 2017

(65) Prior Publication Data
US 2018/0014876 A1 Jan. 18, 2018

Related U.S. Application Data

(60) Provisional application No. 62/362,107, filed on Jul. 14, 2016.

(51) Int. Cl.
*A61B 17/00* (2006.01)
*A61B 18/14* (2006.01)
(Continued)

(52) U.S. Cl.
CPC ........ *A61B 18/1445* (2013.01); *A61B 17/083* (2013.01); *A61B 17/10* (2013.01);
(Continued)

(58) Field of Classification Search
CPC ... A61B 18/1445; A61B 17/083; A61B 17/10; A61B 17/122; A61B 17/1285;
(Continued)

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 Y 9/2009
DE 2415263 A1 10/1975
(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
(Continued)

*Primary Examiner* — Jaymi E Della
*Assistant Examiner* — Michael R Day
(74) *Attorney, Agent, or Firm* — Carter, DeLuca & Farrell LLP (57) ABSTRACT

A tissue clip including an electrode assembly having first and second electrodes with an insulator disposed therebetween. The electrodes are configured to connect to opposite potentials of an energy source. The electrodes and insulator are deformable to shape the tissue clip to include upper and lower legs with a twisted central portion defined therebetween. The upper leg includes an outer facing portion having one end of the first electrode removably coupled to a first jaw of a forceps and an inner facing portion including an end of the second electrode configured to grasp tissue. The lower leg includes an outer facing portion having an opposite end of the second electrode removably coupled to a second jaw and an inner facing portion that includes the opposite end of the first electrode and is configured to grasp tissue.

15 Claims, 6 Drawing Sheets

(51) Int. Cl.
*A61B 17/122* (2006.01)
*A61B 17/128* (2006.01)
*A61B 17/08* (2006.01)
*A61B 17/10* (2006.01)
*A61B 18/00* (2006.01)

(52) U.S. Cl.
CPC ........ *A61B 17/122* (2013.01); *A61B 17/1285* (2013.01); *A61B 2017/00929* (2013.01); *A61B 2017/00946* (2013.01); *A61B 2018/0063* (2013.01); *A61B 2018/00184* (2013.01); *A61B 2018/1465* (2013.01)

(58) Field of Classification Search
CPC ........... A61B 2017/00929; A61B 2017/00946; A61B 2018/00184; A61B 2018/0063; A61B 2018/1465; A61B 2017/00668; A61B 2017/0649; A61B 2018/1435; A61B 2018/1437; A61B 17/0682; A61B 17/115; A61B 17/1152; A61B 17/08; A61B 17/128
See application file for complete search history.

(56) References Cited

U.S. PATENT DOCUMENTS

| | | | |
|---|---|---|---|
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,201,900 A * | 4/1993 | Nardella | A61B 17/122 227/902 |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| D384,413 S | 9/1997 | Zlock et al. | |
| H1745 H | 8/1998 | Paraschac | |
| 5,833,700 A * | 11/1998 | Fogelberg | A61B 17/122 606/158 |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| D670,808 S | 11/2012 | Moua et al. | |
| D680,220 S | 4/2013 | Rachlin | |
| 9,084,608 B2 | 7/2015 | Larson et al. | |
| 9,211,657 B2 | 12/2015 | Ackley et al. | |
| 9,750,522 B2 * | 9/2017 | Scheib | A61B 17/064 |
| 2004/0087987 A1 * | 5/2004 | Rosenberg | A61B 17/12 606/157 |
| 2012/0059394 A1 * | 3/2012 | Brenner | A61B 1/00087 606/142 |
| 2013/0018364 A1 * | 1/2013 | Chernov | A61B 17/122 606/14 |
| 2014/0221995 A1 | 8/2014 | Guerra et al. | |
| 2014/0221999 A1 | 8/2014 | Cunningham et al. | |
| 2014/0228842 A1 | 8/2014 | Dycus et al. | |
| 2014/0230243 A1 | 8/2014 | Roy et al. | |
| 2014/0236149 A1 | 8/2014 | Kharin et al. | |
| 2014/0243811 A1 | 8/2014 | Reschke et al. | |
| 2014/0243824 A1 | 8/2014 | Gilbert | |
| 2014/0249528 A1 | 9/2014 | Hixson et al. | |
| 2014/0250686 A1 | 9/2014 | Hempstead et al. | |
| 2014/0257274 A1 | 9/2014 | McCullough, Jr. et al. | |
| 2014/0257283 A1 | 9/2014 | Johnson et al. | |
| 2014/0257284 A1 | 9/2014 | Artale | |
| 2014/0257285 A1 | 9/2014 | Moua | |
| 2014/0276803 A1 | 9/2014 | Hart | |
| 2014/0284313 A1 | 9/2014 | Allen, IV et al. | |
| 2014/0288549 A1 | 9/2014 | McKenna et al. | |
| 2014/0288553 A1 | 9/2014 | Johnson et al. | |
| 2014/0330308 A1 | 11/2014 | Hart et al. | |
| 2014/0336635 A1 | 11/2014 | Hart et al. | |
| 2014/0353188 A1 | 12/2014 | Reschke et al. | |
| 2015/0018816 A1 | 1/2015 | Latimer | |
| 2015/0025528 A1 | 1/2015 | Arts | |
| 2015/0032106 A1 | 1/2015 | Rachlin | |
| 2015/0051598 A1 | 2/2015 | Orszulak et al. | |
| 2015/0051640 A1 | 2/2015 | Twomey et al. | |
| 2015/0066026 A1 | 3/2015 | Hart et al. | |
| 2015/0080880 A1 | 3/2015 | Sartor et al. | |
| 2015/0080889 A1 | 3/2015 | Cunningham et al. | |
| 2015/0082928 A1 | 3/2015 | Kappus et al. | |
| 2015/0088122 A1 | 3/2015 | Jensen | |
| 2015/0088126 A1 | 3/2015 | Duffin et al. | |
| 2015/0088128 A1 | 3/2015 | Couture | |
| 2015/0094714 A1 | 4/2015 | Lee et al. | |
| 2016/0038226 A1 | 2/2016 | Brandt et al. | |
| 2016/0143687 A1 | 5/2016 | Hart et al. | |

FOREIGN PATENT DOCUMENTS

| | | | |
|---|---|---|---|
| DE | 02514501 A1 | 10/1976 | |
| DE | 2627679 A1 | 1/1977 | |
| DE | 03423356 C2 | 6/1986 | |
| DE | 03612646 A1 | 4/1987 | |
| DE | 3627221 A1 | 2/1988 | |
| DE | 8712328 U1 | 2/1988 | |
| DE | 04303882 C2 | 2/1995 | |
| DE | 04403252 A1 | 8/1995 | |
| DE | 19515914 C1 | 7/1996 | |
| DE | 19506363 A1 | 8/1996 | |
| DE | 29616210 U1 | 11/1996 | |
| DE | 19608716 C1 | 4/1997 | |
| DE | 19751106 A1 | 5/1998 | |
| DE | 19751108 A1 | 5/1999 | |
| DE | 19946527 C1 | 7/2001 | |

(56) References Cited

FOREIGN PATENT DOCUMENTS

| | | |
|---|---|---|
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 2489320 A2 | 8/2012 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 | 6/2002 |
| WO | 02080793 A1 | 10/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |
| WO | 2011156257 A2 | 12/2011 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000. (6 pages).

Johnson et al. "Evaluation of a Bipolar Electrothermal Vessel Sealing Device in Hemorrhoidectomy" Sales/Product Literature; Jan. 2004. (1 page).

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Results with an Electrothermal Bipolar Vessel Sealer" Surgical Endoscopy (2000) 15:799-801. (4 pages).

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.

(56) References Cited

OTHER PUBLICATIONS

Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001. (1 page).
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003. (15 pages).
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler, Abandoned.
U.S. Appl. No. 09/177,950, filed Oct. 23, 1998; inventor: Randel A. Frazier, abandoned.
U.S. Appl. No. 09/387,883, filed Sep. 1, 1999; inventor: Dale F. Schmaltz, abandoned.
U.S. Appl. No. 09/591,328, filed Jun. 9, 2000; inventor: Thomas P. Ryan, abandoned.
U.S. Appl. No. 12/336,970, filed Dec. 17, 2008; inventor: Paul R. Sremcich, abandoned.
U.S. Appl. No. 14/065,644, filed Oct. 29, 2013; inventor: Reschke, abandoned.
Heniford et al. "Initial Research and Clinical Results with an Electrothermal Bipolar Vessel Sealer" Oct. 1999.
International Search Report for application No. PCT/US2017/038535 dated Sep. 8, 2017.

\* cited by examiner

DEVICES AND METHODS FOR TISSUE SEALING AND MECHANICAL CLIPPING

CROSS REFERENCE TO RELATED APPLICATION

The present application claims the benefit of and priority to U.S. Provisional Application Ser. No. 62/362,107, filed on Jul. 14, 2016, the entire contents of which are incorporated herein by reference.

TECHNICAL FIELD

The present disclosure relates to surgical instruments, and more particularly, to surgical instruments for sealing and clipping tissue.

BACKGROUND

Surgical instruments such as energy-based devices are typically used in conjunction with energy sources (external energy sources or portable energy sources incorporated into the instruments themselves) to apply and control the application of energy to tissue to thermally treat tissue (e.g., heat) to achieve a desired tissue effect. Electrosurgical forceps, for example, utilize both the mechanical clamping action of jaw members thereof and the energy provided by the energy source to heat tissue grasped between the jaw members for achieving a desired tissue effect such as sealing. Typically, after grasped tissue is sealed, a clinician advances a blade through the electrosurgical forceps to sever the sealed tissue while the sealed tissue is disposed between the jaw members.

While typical energy-based tissue seals created with these surgical instruments may provide adequate sealing, it would be advantageous to provide further assurances of the effectiveness of these energy-based tissue seals.

SUMMARY

According to one aspect of the present disclosure, a tissue clip is disclosed that includes an electrode assembly having elongated first and second electrodes including an insulator disposed therebetween. The first electrode is configured to connect to a first potential of an electrosurgical energy source and the second electrode configured to connect to a second potential of the energy source. The electrodes and insulator are deformable to shape the tissue clip to include upper and lower legs and a twisted central portion defined therebetween. In aspects, the tissue clip may be U-shaped or V-shaped.

The upper leg includes an outer facing portion having one end of the first electrode configured to removably and electrically couple to a first jaw member of a forceps and an inner facing portion including an end of the second electrode configured to grasp tissue. The lower leg includes an outer facing portion having an opposite end of the second electrode configured to removably and electrically couple to a second, opposing jaw member of the forceps and an inner facing portion including the opposite end of the first electrode configured to grasp tissue.

In aspects of the present disclosure the first and second electrodes are made from a malleable metal and/or the insulator is made from a malleable, electrically insulative material.

In other aspects of the present disclosure at least one of the inner facing portions of the tissue clip includes one or more stop members disposed thereon configured to control a gap distance between opposing inner facing portions when the tissue clip is deformed.

In aspects of the present disclosure, the outer facing portions of the tissue clip are configured to mechanically interface with inner peripheral surfaces of the first and second jaw members. In other aspects, the tissue clip, once deformed about tissue, is configured to maintain a pressure on the tissue within the range of about 3 kg/cm$^2$ to about 16 kg/cm$^2$.

Still other aspects of the present disclosure include a method of forming a tissue clip including disposing an insulative material between first and second elongated electrodes to create an electrode assembly. The method also includes twisting the electrode assembly along a center portion thereof; and deforming the electrode assembly to form a generally U-shaped or V-shaped configuration having upper and lower legs and the central portion. The upper leg includes an outer facing portion including one end of the first electrode configured to removably and electrically couple to a first jaw member of a forceps and an inner facing portion including an end of the second electrode configured to grasp tissue. The lower leg includes an outer facing portion including an opposite end of the second electrode configured to removably and electrically couple to a second, opposing jaw member of the forceps and an inner facing portion including the opposite end of the first electrode configured to grasp tissue.

Other aspects of the present disclosure include a method of sealing tissue using a tissue clip that includes disposing an insulative material between first and second elongated electrodes to create an electrode assembly. The method also includes twisting the electrode assembly along a center portion thereof; deforming the electrode assembly to form a generally U-shaped configuration having upper and lower legs and the central portion, wherein the upper leg includes an outer portion having one end of the first electrode configured to removably and electrically couple to a first jaw member of a forceps and an inner facing portion including an end of the second electrode configured to grasp tissue and wherein the lower leg includes an outer portion having an opposite end of the second electrode configured to removably and electrically couple to a second, opposing jaw member of the forceps and an inner facing portion including the opposite end of the first electrode configured to grasp tissue; loading the tissue clip into the first and second jaw members; approximating tissue with the jaw members and the tissue clip; closing the jaw members and tissue clip about tissue; energizing the electrodes utilizing an electrosurgical energy source to create a tissue seal; and releasing the tissue clip from the jaw members.

In aspects according to the present disclosure, the energizing the electrodes includes energizing the jaw members. In other aspects, the closing the jaw members and tissue clip about tissue includes actuating a drive rod from a laparoscopic forceps. Still in other aspects, the closing the jaw members and tissue clip about tissue includes closing the jaw members and tissue clip about the tissue under a pressure within the range of about 3 kg/cm2 to about 16 kg/cm2.

Yet in other aspects, the closing the jaw members and tissue clip about tissue includes creating a gap between the opposing inner facing portions of the electrodes. The creating of a gap may include utilizing at least one stop member on at least one inner facing portion of one of the electrodes. The creating of a gap may include utilizing at least one stop member on at least one inner facing portion of one of the electrodes to create a gap within a range of about 0.001 inches to about 0.006 inches between opposing inner facing portions.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Particular embodiments of the present disclosure are described hereinbelow with reference to the accompanying drawings in which like reference numerals designate identical or corresponding elements in each of the several views. As used herein, the term "distal" refers to that portion of the system, device, and/or component(s) thereof, which is farther from the user, while the term "proximal" refers to that portion of the system, device, and/or component(s) thereof, which is closer to the user. In the following description, well-known functions or constructions are not described in detail to avoid obscuring the present disclosure in unnecessary detail.

Surgical systems in accordance with the present disclosure can include endoscopic and/or open surgical instruments such as forceps devices, ultrasonic dissection devices, and/or any other suitable surgical devices. Obviously, different electrical and mechanical connections and considerations apply to each particular type of device; however, the aspects and features of the present disclosure remain generally consistent regardless of the particular device used. For a detailed description of the construction and operation of exemplary surgical devices, reference may be made to U.S. Patent Application Publication No. 2013/0255063, U.S. Patent Application Publication No. 2012/0083786 and/or U.S. Pat. No. 8,444,664, the entirety of each of which is incorporated by reference herein.

In the interest of brevity, surgical systems of the present disclosure will only be described herein in connection with an endoscopic surgical forceps.

Figure 1:
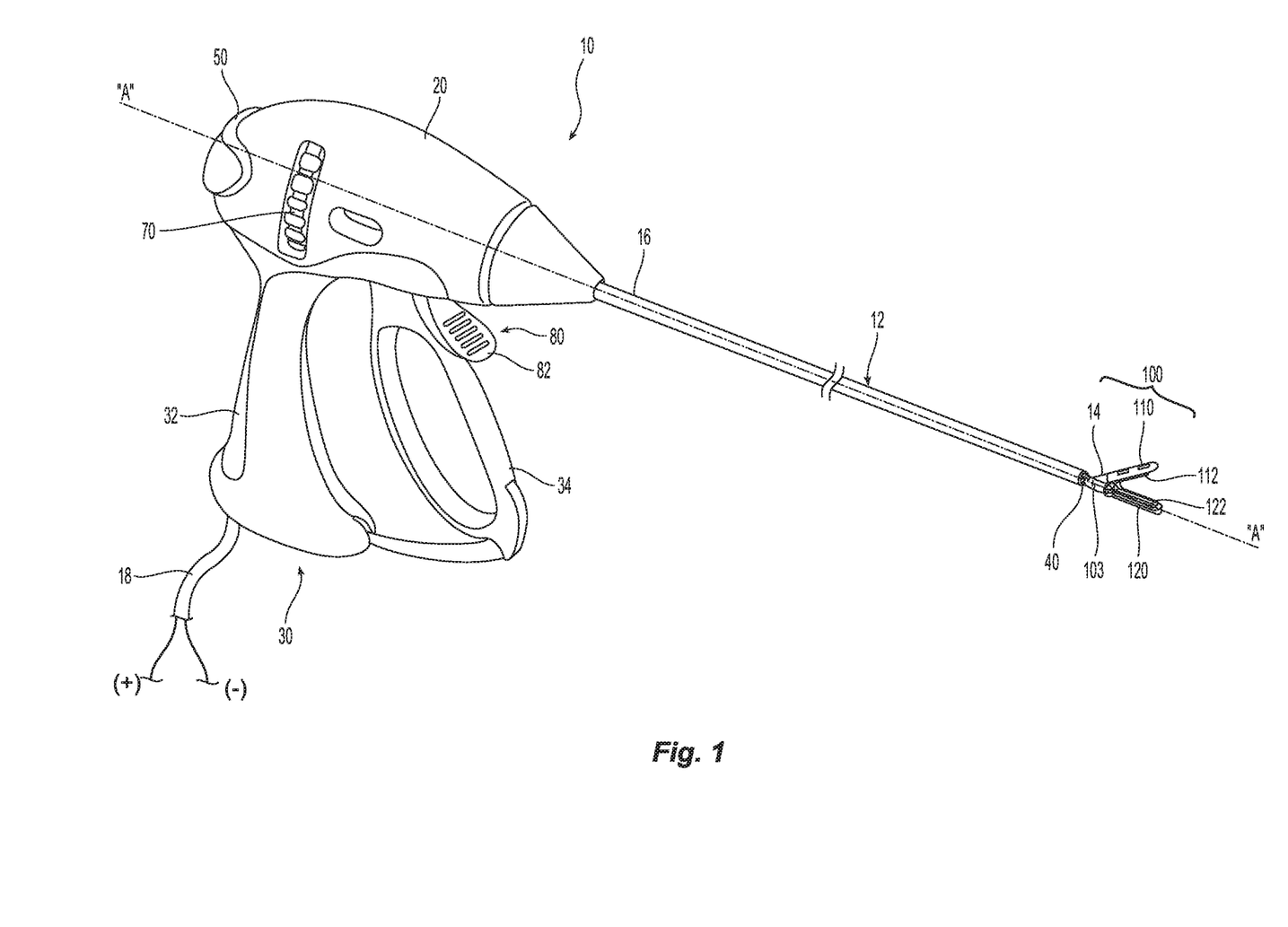
FIG. 1 is a perspective view of a surgical instrument in accordance with the principles of the present disclosure.
Figure 2A:
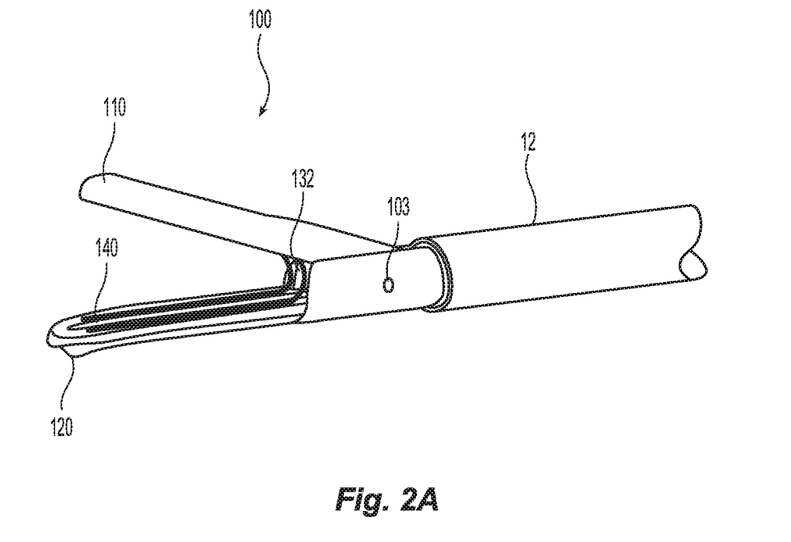
FIG. 2A is an enlarged, side, perspective view of a distal portion of the surgical instrument of FIG. 1 shown with opposing jaw members disposed in an open position.
Figure 2B:
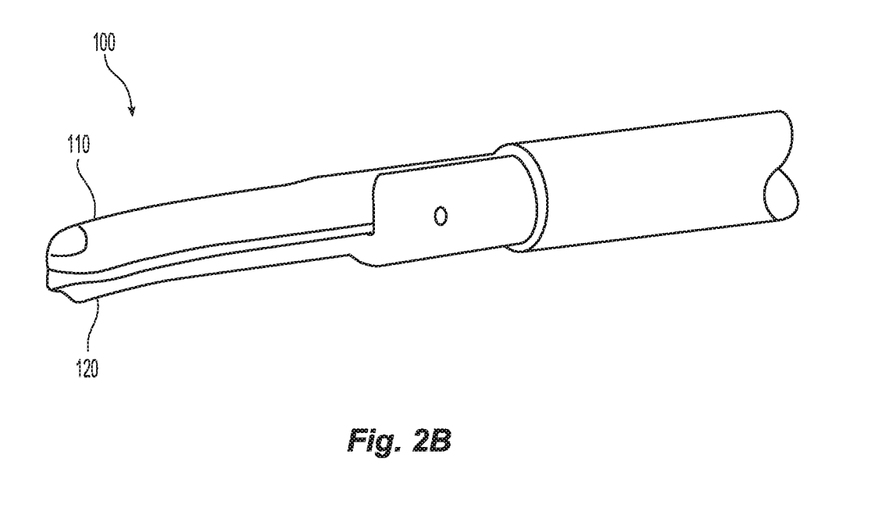
FIG. 2B is an enlarged, side, perspective view of the distal portion of the surgical instrument of FIG. 1 shown in a closed position.

Turning now to FIGS. 1, 2A, and 2B, an electrosurgical endoscopic forceps 10 is provided. Forceps 10 has a longitudinal axis "A-A" defined therethrough, a housing 20, a handle assembly 30, a rotating assembly 70, a trigger assembly 80 and an end effector assembly 100 including first and second jaw members 110 and 120. Jaw members 110 and 120, or portions thereof, may be made from dielectric or insulative materials such as plastic (e.g., thermoplastic, thermosetting plastic, etc.), ceramic material, etc.

The forceps 10 further includes a shaft 12 having a distal end 14 configured to mechanically engage the end effector assembly 100 and a proximal end 16 that mechanically engages the housing 20. The forceps 10 also includes an electrosurgical cable 18 that connects the forceps 10 to a generator 500 (FIG. 3B) or other suitable power source. Alternately, the forceps 10 may be configured as a battery powered instrument. A cable 18, which may include one or more wires, extends through the shaft 12 to provide electrical energy to one or both of the jaw members 110, 120 of end effector assembly 100 as described in greater detail below. The handle assembly 30 supports an electrical switch 50 operatively coupled to the cable 18 to provide electrical energy from the electrosurgical energy source (e.g., generator or battery) to one or both of the jaw members 110, 120 upon actuation of the electrical switch 50.

End effector assembly 100 may be designed as a unilateral assembly, e.g., where the second jaw member 120 is fixed relative to the shaft 12 and the first jaw member 110 is moveable about a pivot 103 relative to the shaft 12 and the second jaw member 120. The handle assembly 30 includes a stationary handle 32 and a movable handle 34 that is operatively coupled to a drive mechanism 40. The movable handle 34 is movable relative to the stationary handle 32 to cause the drive mechanism 40 to pivot the first jaw member 110 about the pivot 103. In some embodiments, the end effector assembly 100 may alternatively be configured as a bilateral assembly, e.g., where both the first and second jaw members 110, 120 are moveable about the pivot 103 relative to one another and to the shaft 12. Other than jaw member 110 being movable and jaw member 120 being stationary, jaw members 110 and 120 are generally identical to one another.

In certain embodiments, the first and second jaw members 110, 120 are configured to move in parallel relation to one another between an open (unapproximated) position and a closed (approximated) position. A knife assembly 130 may be disposed within the shaft 12 and opposing knife channels 112, 122 which are defined within the first and second jaw members 110, 120, respectively, to permit reciprocation of a knife blade 132 (FIG. 2A) of the knife assembly 130 therethrough, e.g., via activation of a trigger 82 of the trigger assembly 80. Knife channels 112, 122 are positioned in vertical registration with one another and cooperate as a unit when jaw members 110, 120 are disposed in a closed (approximated) position to enable reciprocation of the knife blade 132 through the jaw members 110, 120.

Figure 3A:
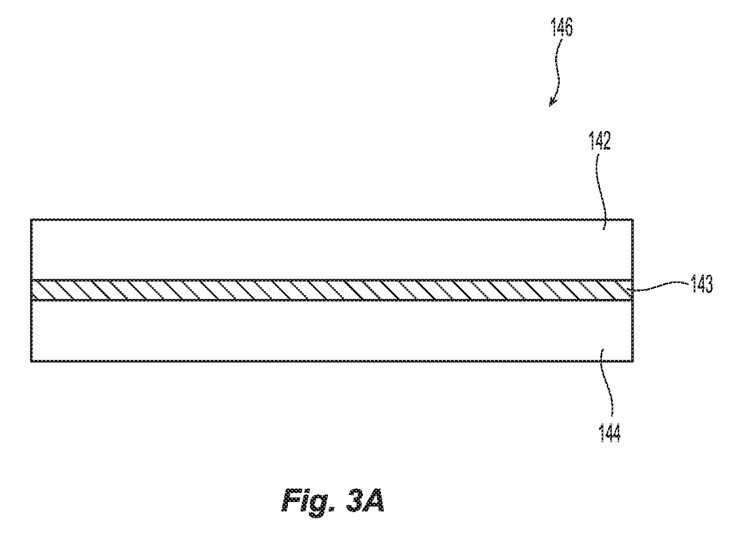
FIG. 3A is an enlarged, perspective view of an elongated electrode assembly for use with the forceps of FIG. 1.
Figure 3B:
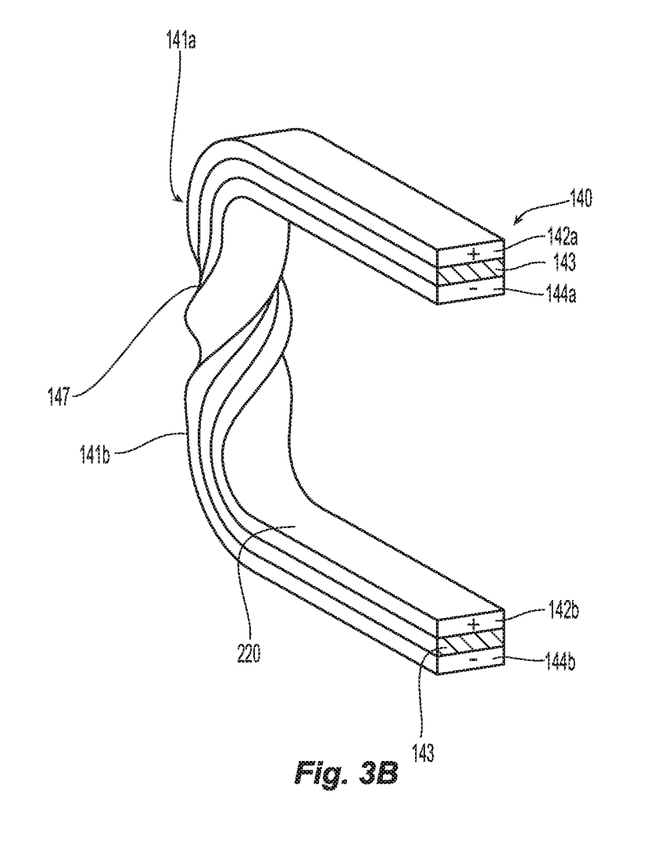
FIG. 3B is an enlarged, side, perspective view of a tissue clip for use with the surgical instrument of FIG. 1 shown in an open position.
Figure 3C:
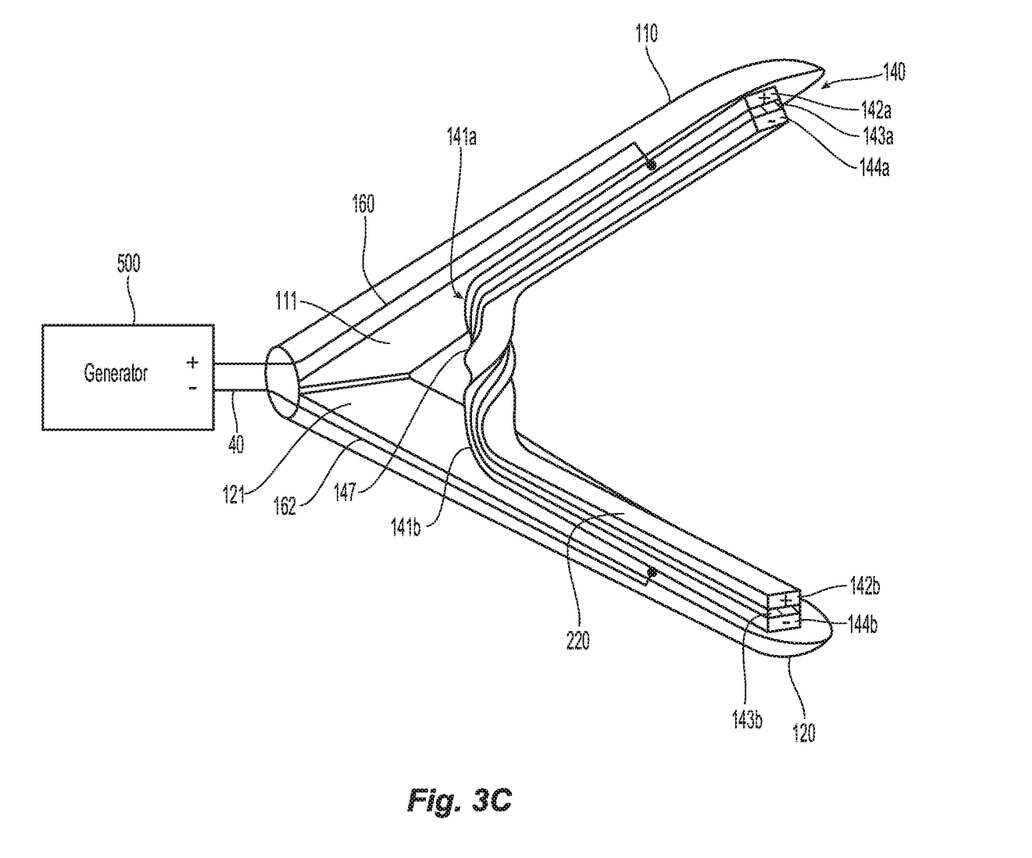
FIG. 3C is an enlarged, side, perspective view of the tissue clip shown mounted within the jaws of the surgical instrument of FIG. 1.
Figure 3D:
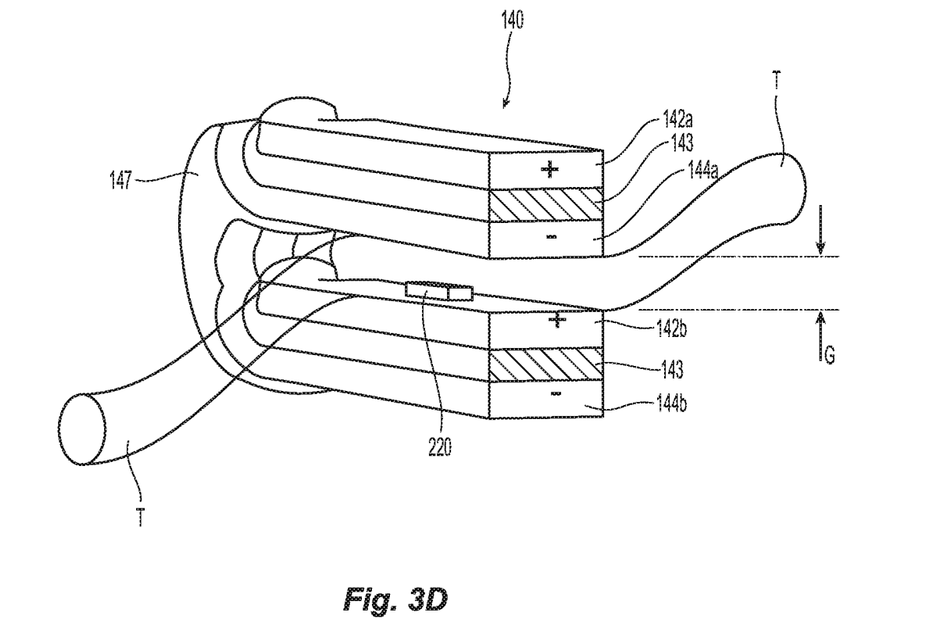
FIG. 3D is an enlarged, side, perspective view of the tissue clip deformed about tissue.

Turning now to FIGS. 3A-3D, a clip 140 may be used to facilitate sealing of tissue "T". More particularly, FIG. 3A shows an electrode assembly including a pair of elongated, malleable electrodes 142 and 144 separated by an insulating material 143, FIG. 3B shows the electrodes 142 and 144 twisted and deformed into a tissue clip 140 which is configured for use with end effector 100 of forceps 10, FIG. 3C shows the tissue clip 140 mounted between jaw members 110 and 120 of the end effector assembly 100 and ready for use, and FIG. 3D shows the tissue clip 140 in the deformed configuration about tissue "T".

As mentioned above, elongated electrodes 142 and 144 are made from a malleable, electrically conductive material to facilitate deformation into a tissue clip 140 for use with vessel sealing. Each electrode 142 and 144 is configured to connect to an electrical energy source, e.g., generator 500, and conduct respective first and second electrical potentials through tissue "T" when held between electrodes 142 and 144. An electrical insulator 143 is disposed between electrodes 142 and 144 and serves to isolate the electrodes 142 and 144 during activation and sealing. Together, electrodes 142 and 144 and insulator 143 form the electrode assembly 146.

In order to form the tissue clip 140 for use with vessel sealing procedures as shown in FIG. 3B, the electrodes 142 and 144 are initially twisted 180 degrees proximate their respective centers 147 and then folded into a generally U-shaped clip 140. Alternatively, the electrodes 142 and 144 could be formed in a U-shape and then twisted or simultaneously twisted and formed. In embodiments, a V-shaped clip may be formed. Once formed, electrode 142 includes upper and lower portions 142a, 142b and electrode 144 includes upper and lower portions 144a, 144b. By initially twisting (or folding then twisting) the electrodes 142 and 144 and forming the tissue clip 140, electrode portion 144a and electrode portion 142b form the inner facing surface of tissue clip 140 which mutually grip tissue when the electrodes 142 and 144 are deformed. Portions 142a and 144b form the outer peripheral surface of clip 140 and are configured to electrically couple to respective first and second electrical potentials via electrical connectors 160 and 162. When mounted within end effector assembly 100 and as shown in FIG. 3B, upper portion 142a releasably engages inner surface 111 of jaw member 110 and once energized, supplies energy to lower portion 142b and lower portion 144b releasably engages inner surface 121 of jaw member 120 and once energized, supplies energy to upper portion 144a. Upper portion 142a and lower portion 144b of tissue clip 140 may include one or more mechanical features to releasably engage the inner peripheral surfaces of respective jaw members 110 and 120.

In use, the movable handle 34 is actuated to enable the first and second jaw members 110, 120 to move from the open position to the closed position to thereby grasp tissue "T" disposed between the first and second jaw members 110, 120 while deforming the tissue clip 140 onto the tissue "T" disposed between the first and second jaw members 110, 120. As the first and second jaw members 110, 120 move toward the closed position, electrode portions 144a and 142b engage tissue "T" such that, upon activation, electrosurgical energy is transmitted through tissue "T" to create a tissue seal. Electrosurgical energy can be supplied to the electrode portions 144a and 142b prior to, during, and/or after deformation of the tissue clip 140 depending upon a particular purpose.

Once deformed about tissue "T" and energized to create a tissue seal, tissue clip 140 may be released from the jaw members 110 and 120 and removed by the surgeon and the tissue "T" may be cut along the tissue seal if desired. Alternatively, tissue clip 140 including electrode 142, electrode 144 and insulation 143 may be made from biodegradable materials that dissolve over time and, in such cases, tissue clip 140 may be left in situ. In embodiments, a second clip (not shown) may be deformed and energized adjacent the initial clip 140 to create a second tissue seal. A knife or cutting element 132 may be utilized to cut the tissue "T" between the two tissue seals.

One or more mechanical interfaces (not shown) may be employed to mount tissue clip 140 within jaw members 110 and 120 respectively, e.g., flanges, snap-like features, grooves, detents, etc. In embodiments, upon deformation, the mechanical interfaces that mount the tissue clip 140 to the jaw members 110 and 120 may likewise deform and automatically release the tissue clip 140 once fully deformed. In other embodiments, one or more of the mechanical interfaces may automatically reset after deformation and release of the tissue clip 140 to facilitate alignment and mounting a second or additional tissue clips 140. Yet in other embodiments, the tissue clip 140 is simply retained within the jaw members 110 and 120 via friction-fit engagement.

In embodiment, the tissue clip 140 may be mounted within the jaw members 110 and 120 in a skewed of laterally offset orientation such that the knife channels 112 and 122 are exposed. Once the tissue clip 140 is deformed and energized about tissue "T", the knife blade 132 may be advanced along the side of the tissue clip 140 to cut the tissue "T" (or vessel). In this scenario, the tissue clip 140 is intended for use as an end clip when the opposite end of the tissue "T" is being removed. Alternatively, this jaw member 110 and 120 and tissue clip 140 arrangement may be utilized between two clips and the knife blade 132 may be advanced to sever tissue disposed between the two tissue clips once deformed and a seal is created on either side of the tissue "T". Clip may also include one or more channels (not shown) defined therein that allow the knife 132 to translate through the tissue clip 140 once the tissue clip 140 is deformed.

Any of the presently disclosed clips can be formed of any suitable bio-compatible material. In some embodiments, any of the presently disclosed clips, or portions thereof, may be formed of a dielectric material. In certain embodiments, any of the presently disclosed clips, or portions thereof, may be formed of an electrically conductive material, whereby any of the presently disclosed clips may be utilized as an electrical conduit (e.g., via any of the presently described tissue-contacting surfaces) for conducting electrically energy directly and/or indirectly to tissue "T" to facilitate sealing of the tissue "T."

Any of the presently described jaw members 110 and 120, or portions thereof, may be made include dielectric or insulative material such as plastic (e.g., thermoplastic, thermosetting plastic, etc.), ceramic material, etc.

In some embodiments, one or more stop members 220 may be included on any of the presently described tissue-contacting portions of electrodes 144a, 142b (inner portions of the tissue clip 140). The stop members 220 may be made from insulative, non-conductive or conductive materials depending upon a particular purpose and depending upon the particular configuration of stop members 220 and various applicable electrical considerations. Such stop members 220 may function to provide a specific gap distance "G" between the tissue contacting portions 144a and 142b of the electrodes 144 and 142b when the tissue clip 140 is deformed which prevents the tissue-contacting portions 144a and 142b from contacting one another during the transmission of electrical energy and provides for a higher quality seal. In embodiments, the gap "G" is within a range of about 0.001 inches to about 0.006 inches.

In embodiments, the forceps 10 may be configured to close the jaw members 110 and 120 and the tissue clip 140 about tissue under a particular closure pressure within the range of about 3 kg/cm² to about 16 kg/cm². Once deformed and released from the jaw members 110 and 120, the tissue clip 140 may be designed to maintain the closure pressure within the above pressure range while deformed.

A method of forming a tissue clip 140 is also disclosed and includes disposing an insulative material 143 between first and second elongated electrodes 142 and 144 to create an electrode assembly 146. The method also includes twisting the electrode assembly 146 along a center portion 147 thereof; and deforming the electrode assembly 146 to form a generally U-shaped or V-shaped configuration having upper and lower legs 141a and 141b and the central portion 147. The upper leg 141a includes an outer facing portion including one end of the first electrode 142a configured to removably and electrically couple to a first jaw member 110 of a forceps 10 and an inner facing portion including an end of the second electrode 144a configured to grasp tissue. The lower leg 141b includes an outer facing portion including an opposite end of the second electrode 144b configured to removably and electrically couple to a second, opposing jaw member 120 of the forceps 10 and an inner facing portion including the opposite end of the first electrode 142b configured to grasp tissue.

A method of sealing tissue using a tissue clip 140 is also disclosed herein and includes disposing an insulative material 143 between first and second elongated electrodes 142 and 144 to create an electrode assembly 146. The method also includes twisting the electrode assembly 146 along a center portion 147 thereof; deforming the electrode assembly 146 to form a generally U-shaped configuration having upper and lower legs 141a and 141b, respectively, and the central portion 147, wherein the upper leg 141a includes an outer portion having one end of the first electrode 142 configured to removably and electrically couple to a first jaw member 110 of a forceps 10 and an inner facing portion including an end of the second electrode 144a configured to grasp tissue, the lower leg 141b including an outer portion having an opposite end of the second electrode 144b configured to removably and electrically couple to a second, opposing jaw member 120 of the forceps 10 and an inner facing portion including the opposite end of the first electrode 142b configured to grasp tissue; loading the tissue clip 140 into the first and second jaw members 110 and 120, respectively; approximating tissue with the jaw members 110 and 120 and the tissue clip 140; closing the jaw members 110 and 120 and tissue clip 140 about tissue; energizing the electrodes 142 and 144 utilizing an electrosurgical energy source 500 to create a tissue seal; and releasing the tissue clip 140 from the jaw members 110 and 120.

Energizing the electrodes 142 and 144 may include energizing the jaw members 110 and 120 which, in turn, energize the upper and lower legs 141a and 141b of the tissue clip 140. The closing the jaw members 110 and 120 and tissue clip 140 about tissue includes actuating a drive rod 40 from forceps 10. The closing of the jaw members 110 and 120 and tissue clip 140 about tissue "T" may include closing the jaw members 110 and 120 and tissue clip 140 about the tissue under a pressure within the range of about 3 kg/cm² to about 16 kg/cm².

In embodiments, the closing the jaw members 110 and 120 and tissue clip 140 about tissue includes creating a gap "G" between the opposing inner facing portions 144a and 142b of the electrodes 142 and 144. The creating of a gap "G" may include utilizing at least one stop member 220 on at least one inner facing portion of one of the electrodes, e.g., portion 142b. The creating of a gap "G" may include utilizing at least one stop member 220 on at least one inner facing portion of one of the electrodes, e.g., portion 142b, to create a gap "G" within a range of about 0.001 inches to about 0.006 inches between opposing inner facing portions 142b and 144a.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 4:
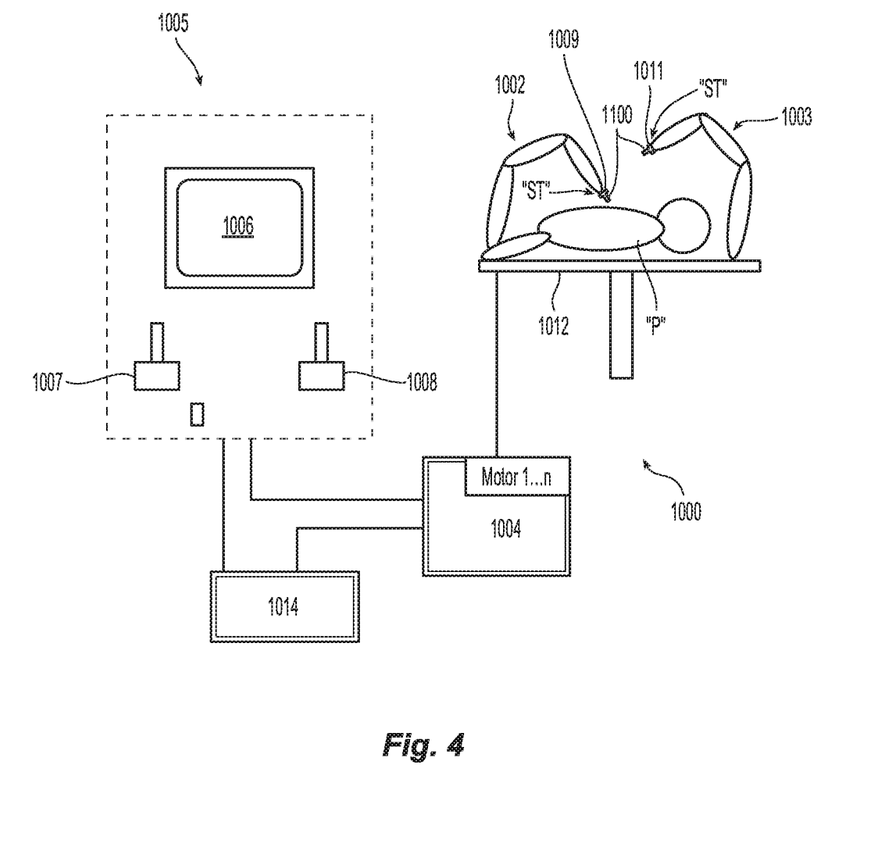
FIG. 4 is a schematic illustration of a medical work station and operating console in accordance with the present disclosure.

Referring also to FIG. 4, a medical work station is shown generally as work station 1000 and generally may include a plurality of robot arms 1002, 1003; a control device 1004; and an operating console 1005 coupled with the control device 1004. The operating console 1005 may include a display device 1006, which may be set up in particular to display three-dimensional images; and manual input devices 1007, 1008, by means of which a person (not shown), for example a clinician, may be able to telemanipulate the robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100 (e.g., a pair of jaw members), in accordance with any one of several embodiments disclosed herein, as will be described in greater detail below.

The robot arms 1002, 1003 may be driven by electric drives (not shown) that are connected to the control device 1004. The control device 1004 (e.g., a computer) may be set up to activate the drives, in particular by means of a computer program, in such a way that the robot arms 1002, 1003, their attaching devices 1009, 1011 and thus the surgical tool (including the end effector 1100) execute a desired movement according to a movement defined by means of the manual input devices 1007, 1008. The control device 1004 may also be set up in such a way that it regulates the movement of the robot arms 1002, 1003 and/or of the drives.

The medical work station 1000 may be configured for use on a patient "P" lying on a patient table 1012 to be treated in a minimally invasive manner by means of the end effector 1100. The medical work station 1000 may also include more than two robot arms 1002, 1003, the additional robot arms likewise connected to the control device 1004 and telemanipulatable by means of the operating console 1005. A medical instrument or surgical tool (including an end effector 1100) may also be attached to the additional robot arm. The medical work station 1000 may include a database 1014 coupled with the control device 1004. In some embodiments, pre-operative data from patient/living being "P" and/or anatomical atlases may be stored in the database 1014.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A tissue clip, comprising:
an electrode assembly including elongated first and second electrodes having an insulator disposed therebetween, the first electrode configured to connect to a first potential of an electrosurgical energy source and the second electrode configured to connect to a second potential of the energy source, the electrodes and insulator deformable to shape the tissue clip including upper and lower legs and a twisted central portion defined therebetween,
wherein the upper leg includes an outer facing portion having one end of the first electrode configured to removably and electrically couple to a first jaw member of a forceps and an inner facing portion including an end of the second electrode configured to grasp tissue, the lower leg including an outer facing portion having an opposite end of the second electrode configured to removably and electrically couple to a second, opposing jaw member of the forceps and an inner facing portion including the opposite end of the first electrode configured to grasp tissue.

2. A tissue clip according to claim 1 wherein the first and second electrodes are made from a malleable metal.

3. A tissue clip according to claim 1 wherein the insulator is made from a malleable, electrically insulative material.

4. A tissue clip according to claim 1 wherein at least one of the inner facing portions of the tissue clip includes a stop member disposed thereon configured to control a gap distance between opposing inner facing portions when the tissue clip is deformed.

5. A tissue clip according to claim 1 wherein the tissue clip is U-shaped.

6. A tissue clip according to claim 1 wherein the outer facing portions of the tissue clip are configured to mechanically interface with inner peripheral surfaces of respective first and second jaw members.

7. A tissue clip according to claim 1 wherein, once deformed about tissue, the tissue clip is configured to maintain a pressure on the tissue within the range of about 3 kg/cm$^2$ to about 16 kg/cm$^2$.

8. A method of forming a tissue clip, comprising:
disposing an insulative material between first and second elongated electrodes to create an electrode assembly;
twisting the electrode assembly along a center portion thereof; and
deforming the electrode assembly to form a generally U-shaped configuration having upper and lower legs and the central portion, wherein the upper leg includes an outer facing portion having one end of the first electrode configured to removably and electrically couple to a first jaw member of a forceps and an inner facing portion including an end of the second electrode configured to grasp tissue, the lower leg including an outer facing portion having an opposite end of the second electrode configured to removably and electrically couple to a second, opposing jaw member of the forceps and an inner facing portion including the opposite end of the first electrode configured to grasp tissue.

9. A method of sealing tissue using a tissue clip, comprising:
disposing an insulative material between first and second elongated electrodes to create an electrode assembly;
twisting the electrode assembly along a center portion thereof;
deforming the electrode assembly to form a generally U-shaped configuration having upper and lower legs and the central portion, wherein the upper leg includes an outer portion having one end of the first electrode configured to removably and electrically couple to a first jaw member of a forceps and an inner facing portion including an end of the second electrode configured to grasp tissue, the lower leg including an outer portion having an opposite end of the second electrode configured to removably and electrically couple to a second, opposing jaw member of the forceps and an inner facing portion including the opposite end of the first electrode configured to grasp tissue;
loading the tissue clip into the first and second jaw members;
approximating tissue with the jaw members and the tissue clip;

closing the jaw members and tissue clip about tissue;
energizing the electrodes utilizing an electrosurgical energy source to create a tissue seal; and
releasing the tissue clip from the jaw members.

10. A method according to claim 9 wherein the energizing the electrodes includes energizing the jaw members.

11. A method according to claim 9 wherein the closing the jaw members and tissue clip about tissue includes actuating a drive rod from a laparoscopic forceps.

12. A method according to claim 9 wherein the closing the jaw members and tissue clip about tissue includes closing the jaw members and tissue clip about the tissue under a pressure within the range of about 3 kg/cm$^2$ to about 16 kg/cm$^2$.

13. A method according to claim 9 wherein the closing the jaw members and tissue clip about tissue includes creating a gap between the opposing inner facing portions of the electrodes.

14. A method according to claim 13 wherein the creating a gap includes utilizing at least one stop member on at least one inner facing portion of one of the electrodes.

15. A method according to claim 13 wherein the creating a gap includes utilizing at least one stop member on at least one inner facing portion of one of the electrodes to create a gap within a range of about 0.001 inches to about 0.006 inches between opposing inner facing portions.

* * * * *